US012690998B2

(12) United States Patent
Falcon et al.

(10) Patent No.: US 12,690,998 B2
(45) Date of Patent: Jul. 28, 2026

(54) URINE COLLECTION AND DRAINAGE APPARATUS

(71) Applicants: Yoani Falcon, Orlando, FL (US);
Barbara Valdez Hernandez, Orlando,
FL (US)

(72) Inventors: Yoani Falcon, Orlando, FL (US);
Barbara Valdez Hernandez, Orlando,
FL (US)

( * ) Notice: Subject to any disclaimer, the term of this
patent is extended or adjusted under 35
U.S.C. 154(b) by 460 days.

(21) Appl. No.: 18/205,341

(22) Filed: Jun. 2, 2023

(65) Prior Publication Data

US 2024/0398607 A1 Dec. 5, 2024

(51) Int. Cl.
*A61F 5/451* (2006.01)
*A61F 13/15* (2006.01)

(52) U.S. Cl.
CPC .............. *A61F 5/451* (2013.01); *A61F 13/15*
(2013.01); *A61F 2013/15146* (2013.01)

(58) Field of Classification Search
CPC .......... A61F 5/451; A61F 5/455; A61F 13/15;
A61F 2013/15146; A61F 2013/4506
See application file for complete search history.

(56) References Cited

U.S. PATENT DOCUMENTS

| | | | |
|---|---|---|---|
| 4,610,675 A | | 9/1986 | Triunfol |
| 4,747,166 A | * | 5/1988 | Kuntz ..................... A61F 5/455 |
| | | | 4/144.1 |
| 5,678,564 A | * | 10/1997 | Lawrence ................ A61F 5/455 |
| | | | 600/573 |
| D437,409 S | | 2/2001 | Fujioka |
| 7,220,250 B2 | * | 5/2007 | Suzuki ..................... A61F 5/451 |
| | | | 604/328 |
| 7,390,320 B2 | | 6/2008 | Machida |
| 7,695,460 B2 | * | 4/2010 | Wada ....................... A61F 5/451 |
| | | | 604/326 |
| 7,939,706 B2 | * | 5/2011 | Okabe ................... A61F 5/4404 |
| | | | 604/361 |
| 11,504,265 B2 | | 11/2022 | Godinez |
| 11,839,528 B2 | * | 12/2023 | Townsend ........... A61F 13/0209 |
| 12,350,190 B2 | * | 7/2025 | Hughett, Sr. ......... A61F 5/4556 |
| 2001/0037097 A1 | * | 11/2001 | Cheng ..................... A61F 5/455 |
| | | | 4/144.1 |
| 2011/0060300 A1 | * | 3/2011 | Weig ....................... A61F 5/451 |
| | | | 604/319 |
| 2022/0265461 A1 | | 8/2022 | Kharkar |
| 2022/0330709 A1 | | 10/2022 | Faraggi |

FOREIGN PATENT DOCUMENTS

EP          1504737          9/2005

* cited by examiner

*Primary Examiner* — Jessica Arble
*Assistant Examiner* — Hans Kaliher

(57) ABSTRACT

A urine collection and drainage apparatus for draining urine
from an individual includes a liner with a top surface and a
bottom surface and being elongated between a pair of ends.
A pad is coupled to the top surface of the liner, and a drain
tube extends through the liner and the pad. The drain tube is
in fluid communication with a top side of the pad, and the
drain tube has an open distal end with respect to the pad
which has a size such that the open distal end is configured
for inserting into an adapter of a suction device such that the
drain tube is in fluid communication with the suction device.

5 Claims, 5 Drawing Sheets

URINE COLLECTION AND DRAINAGE APPARATUS

BACKGROUND OF THE INVENTION

(1) Field of the Invention

The disclosure relates to urine drainage apparatuses and more particularly pertains to a new urine drainage apparatus for draining urine from an individual.

(2) Description of Related Art Including Information Disclosed Under 37 CFR 1.97 and 1.98

The prior art described urine drainage apparatuses which use an absorbent pad to collect urine from a user and a suction device to draw the urine from the absorbent pad. However, the prior art does not disclose such an apparatus which includes a drain tube which extends through said absorbent pad so that urine may be collected without first being absorbed by the pad.

BRIEF SUMMARY OF THE INVENTION

An embodiment of the disclosure meets the needs presented above by generally comprising a liner with a top surface and a bottom surface and being elongated between a pair of ends. A pad is coupled to the top surface of the liner, and a drain tube extends through the liner and the pad. The drain tube is in fluid communication with a top side of the pad, and the drain tube has an open distal end with respect to the pad which has a size such that the open distal end is configured for inserting into an adapter of a suction device such that the drain tube is in fluid communication with the suction device.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
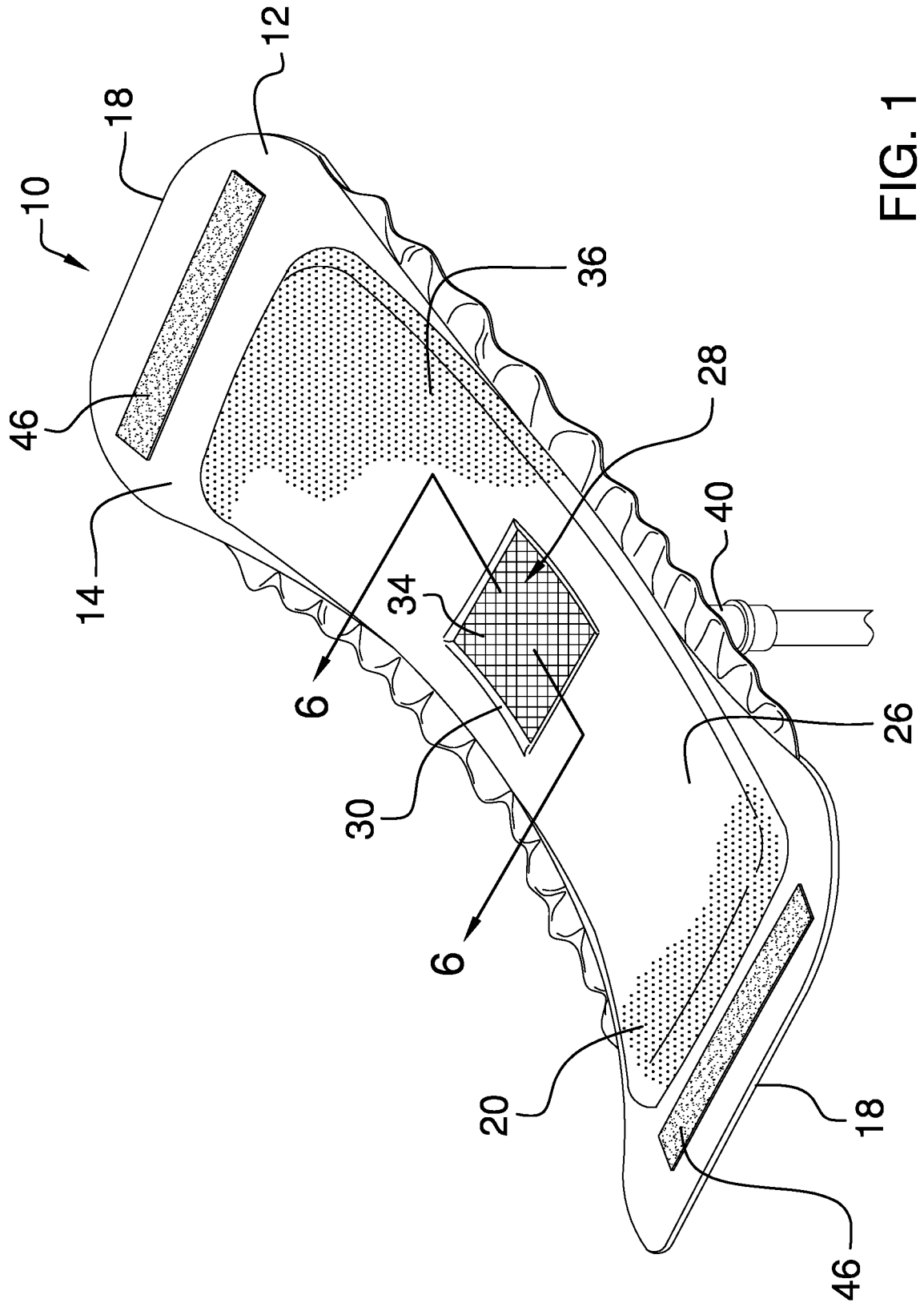
FIG. 1 is a perspective view of a urine collection and drainage apparatus according to an embodiment of the disclosure.
Figure 2:
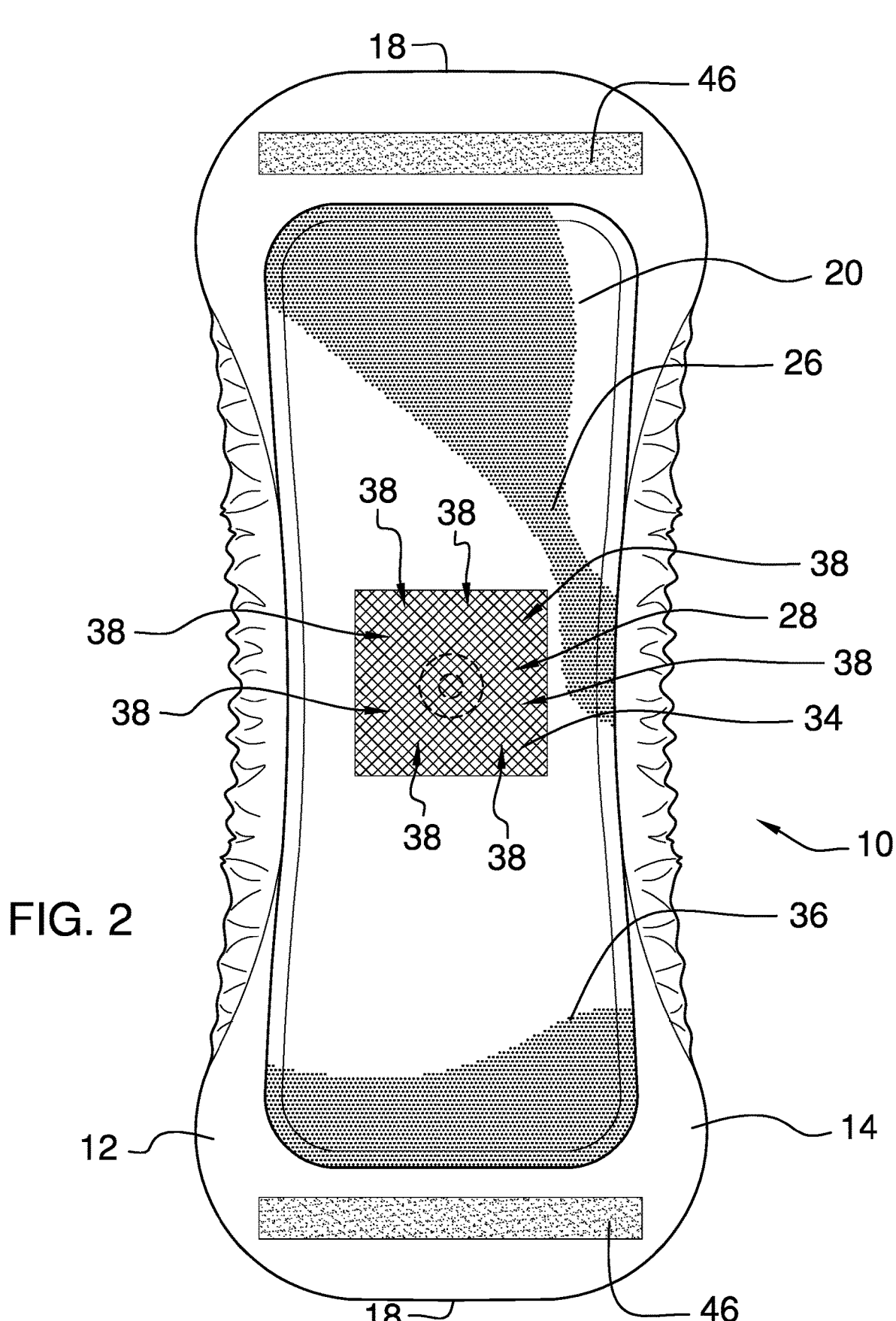
FIG. 2 is a top view of an embodiment of the disclosure.
Figure 3:
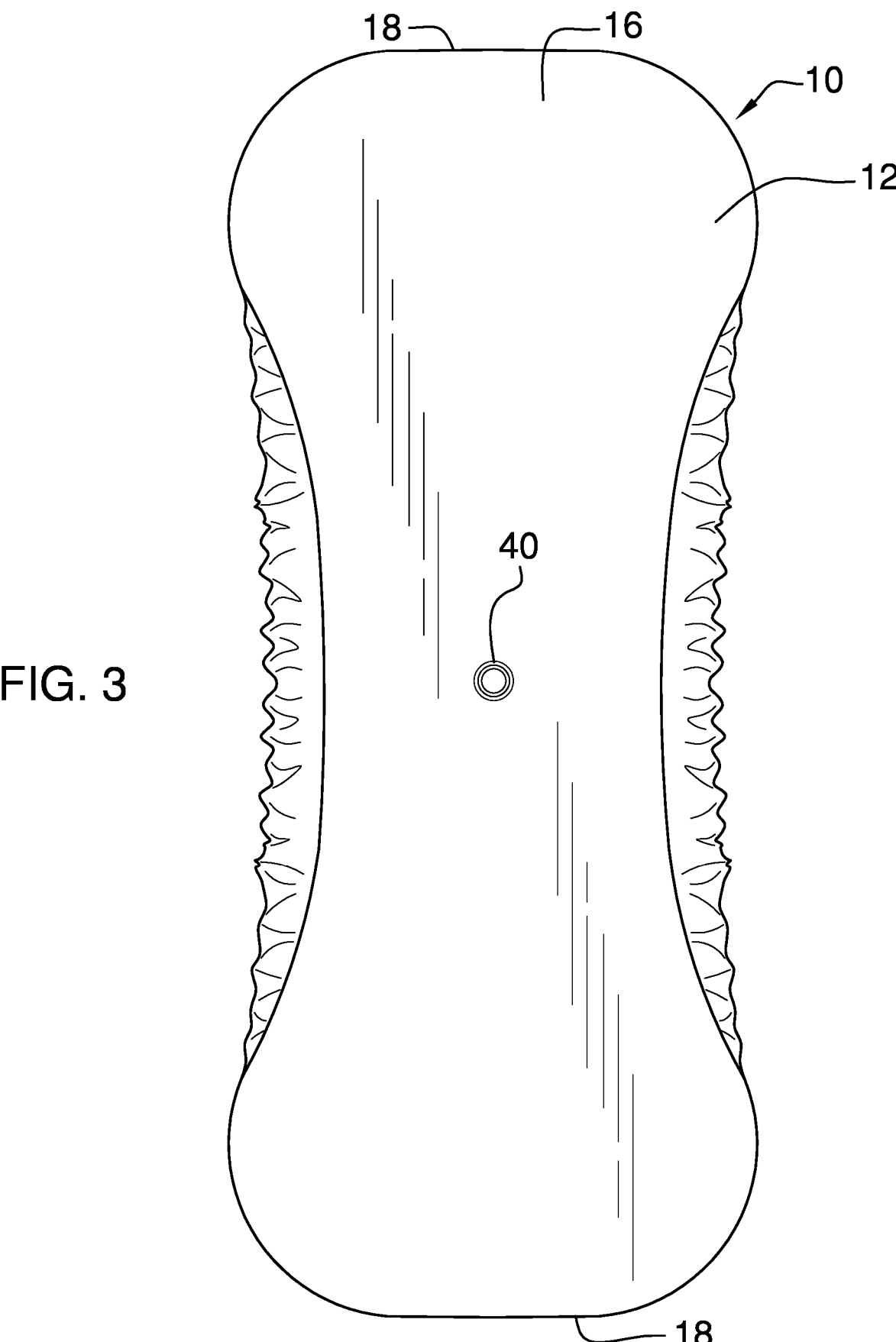
FIG. 3 is a bottom view of an embodiment of the disclosure.
Figures 4, 5:
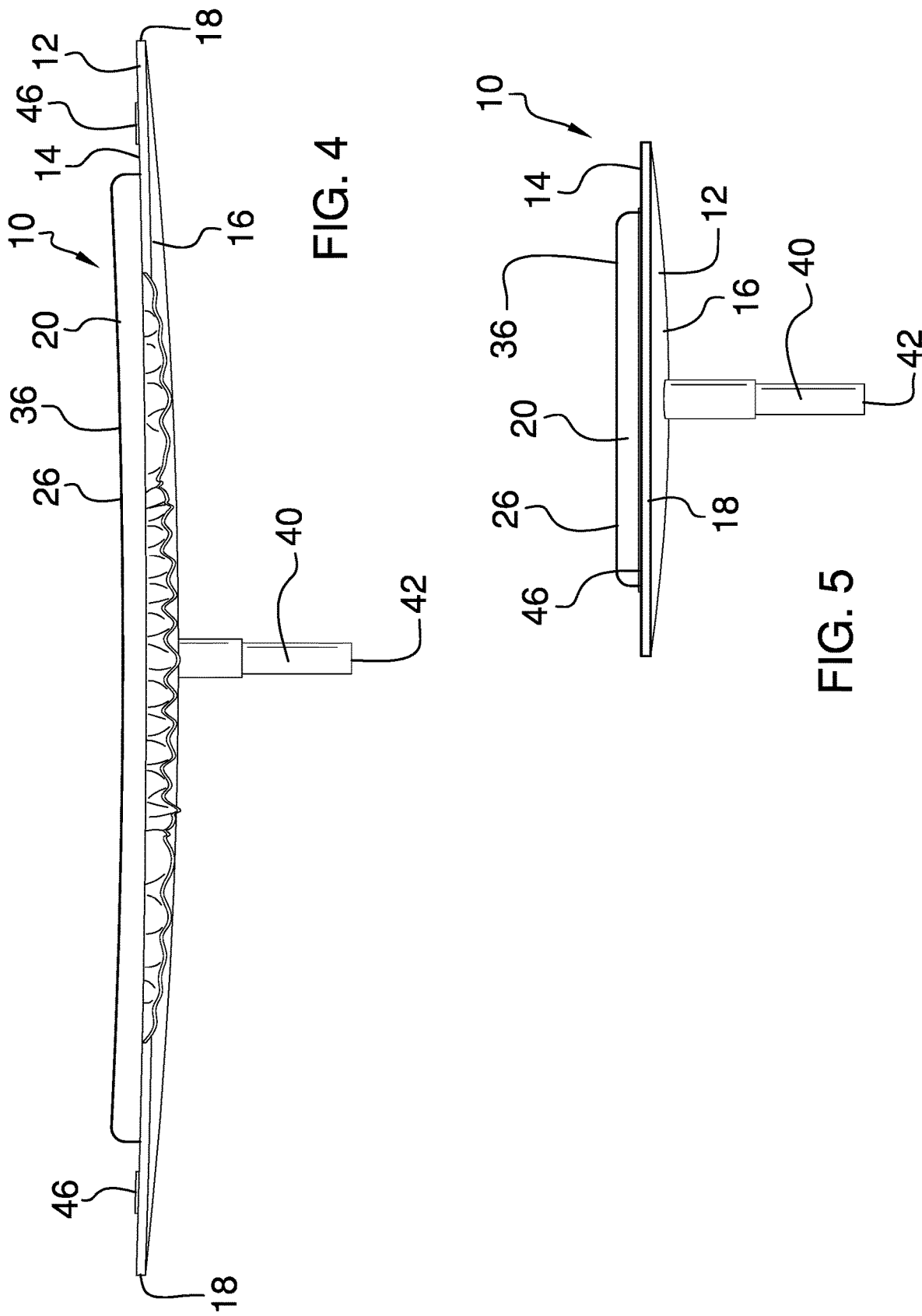
FIG. 4 is a side view of an embodiment of the disclosure.
FIG. 5 is a front view of an embodiment of the disclosure.
Figure 6:
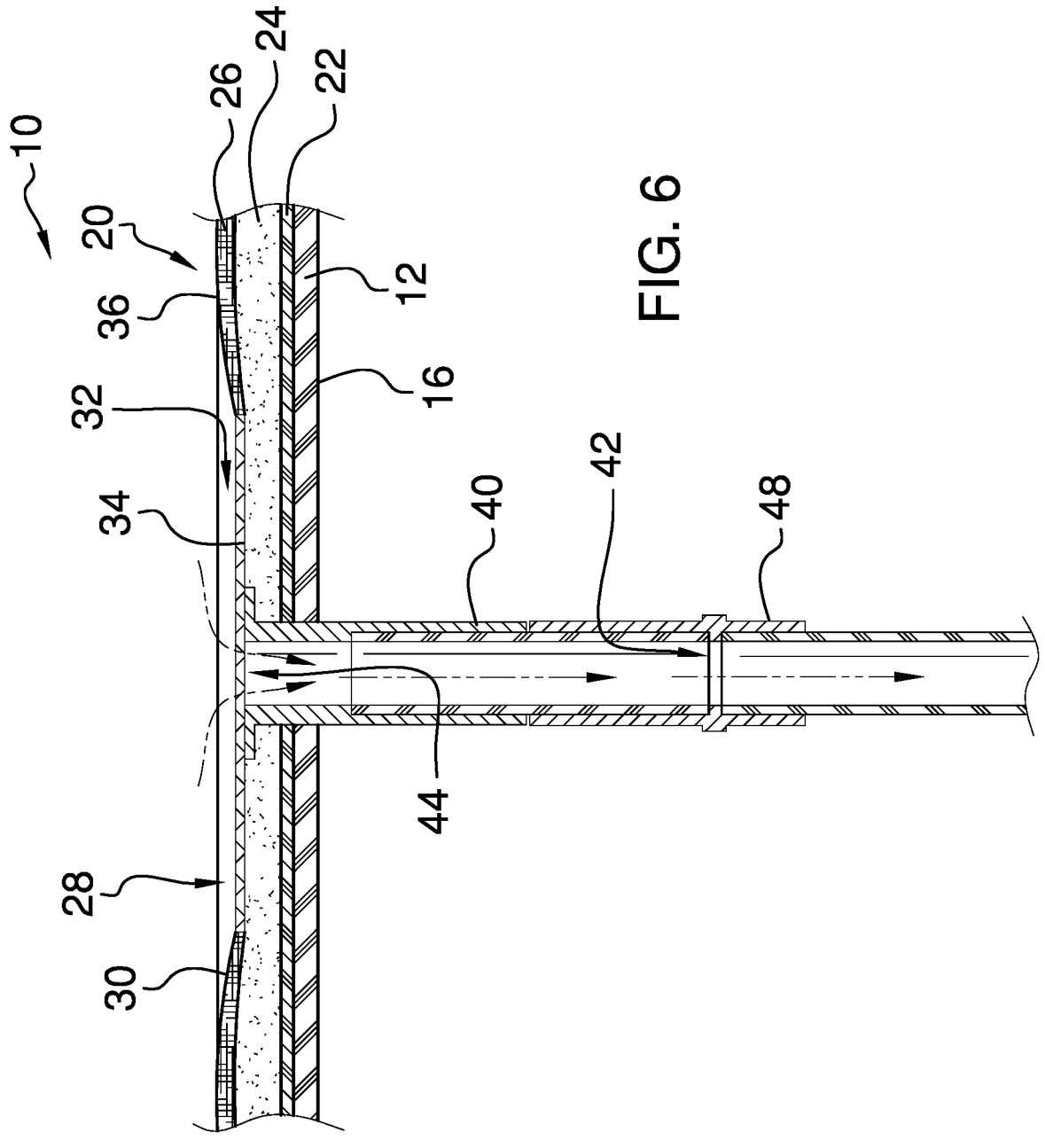
FIG. 6 is a cross-section view of an embodiment of the disclosure taken from Arrows 6-6 in FIG. 1.

With reference now to the drawings, and in particular to FIGS. 1 through 6 thereof, a new urine drainage apparatus embodying the principles and concepts of an embodiment of the disclosure and generally designated by the reference numeral 10 will be described.

As best illustrated in FIGS. 1 through 6, the urine collection and drainage apparatus 10 generally comprises a liner 12 having a top surface 14 and a bottom surface 16 and being elongated between a pair of ends 18. A pad 20 is coupled to the top surface 14 of the liner 12. The pad 20 comprises a fluid-impermeable layer 22, an absorbent layer 24, and a fluid-permeable layer 26. The fluid-impermeable layer 22 is configured to prevent urine from a user from leaking therethrough. The absorbent layer 24 is positioned above the fluid-impermeable layer 22 and is configured for absorbing the urine. The absorbent layer 24 comprises a cellulose gel. A fluid-permeable layer 26 is positioned above the absorbent layer 24 and is configured for permitting the urine to pass therethrough. The fluid-permeable layer 26 has an aperture 28 extending therethrough which is centered between the pair of ends 18 of the liner 12 and has a square shape. The fluid-permeable layer 26 has an inner boundary region 30 surrounding the aperture 28. The inner boundary region 30 is angled downwardly toward the aperture 28 to form a cavity 32 above and in fluid communication with the aperture 28.

A filter 34 is coupled to the pad 20 and is positioned in the aperture 28. The filter 34 is inset downwardly from a top side 36 of the pad 20. The filter 34 has a plurality of openings 38 extending therethrough, each of which has a size such that the filter 34 is configured to permit the urine to pass through the filter 34 and prevent the cellulose gel from passing through the filter 34.

A drain tube 40 extends through the liner 12 and the pad 20 and is in fluid communication with the top side 36 of the pad 20. The drain tube 40 has an open distal end 42 with respect to the pad 20 which has a size such that the open distal end 42 is configured for inserting into an adapter 48 of a suction device such that the drain tube 40 is in fluid communication with the suction device. The drain tube 40 extends through the fluid-impermeable layer 22 and the absorbent layer 24 and has an open proximal end 44 with respect to the pad 20 which is positioned in abutment with and below the filter 34.

A pair of adhesives 46 is coupled to the liner 12. Each adhesive 46 of the pair of adhesives 46 is positioned adjacent to an associated one of the pair of ends 18 of the liner 12. Each adhesive 46 of the pair of adhesives 46 may comprise silicone or any other conventional adhesive 46 material.

In use, the urine collection and drainage apparatus 10 with the pad 20 adjacent to a user's groin, and the suction device is attached to the open distal end 42 of the tube via the adapter 48. The boundary region of the fluid-permeable layer 26 is shaped such that the filter 34 and drain tube 40 are spaced downwardly away from the user, which prevents obstruction of the filter 34 and drain tube 40. The aperture 28 of the fluid-permeable layer 26 is positioned such that urine from the user is directed primarily through the filter 34 and into the drain tube 40. The suction device is activated to urge urine through the filter 34 and the drain tube 40 to a storage reservoir of the suction device. Stray portions of urine which are not directed through the filter 34 are absorbed by the absorbent layer 24 of the pad 20.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A urine collection and drainage apparatus comprising:
a liner having a top surface and a bottom surface, the liner being elongated between a pair of ends;
a pad being coupled to the top surface of the liner;
a drain tube extending through the liner and the pad, the drain tube being in fluid communication with a top side of the pad, the drain tube having an open distal end with respect to the pad, the open distal end having a size such that the open distal end is configured for inserting into an adapter of a suction device such that the drain tube is in fluid communication with the suction device;
wherein the pad comprises:
a fluid-impermeable layer being configured to prevent urine from a user from leaking therethrough; and
an absorbent layer being positioned above the fluid-impermeable layer, the absorbent layer being configured for absorbing the urine;
the drain tube extends through the fluid-impermeable layer and the absorbent layer;
wherein the pad further comprises a fluid-permeable layer being positioned above the absorbent layer, the fluid-permeable layer being configured for permitting the urine to pass therethrough;
wherein the absorbent layer comprises a cellulose gel;
a filter being coupled to the pad, the filter being positioned in an aperture extending through the fluid-permeable layer, the filter having a plurality of openings extending therethrough, each opening of the plurality of openings having a size such that the filter is configured to permit the urine to pass through the filter and prevent the cellulose gel from passing through the filter; and
wherein the drain tube has an open proximal end with respect to the pad being positioned in abutment with and below the filter.

2. The apparatus of claim 1, wherein:
the fluid-permeable layer has an inner boundary region surrounding the aperture, the inner boundary region being angled downwardly toward the aperture to form a cavity above and in fluid communication with the aperture; and
the filter is inset downwardly from the top side of the pad.

3. The apparatus of claim 1, wherein the aperture is centered between the pair of ends of the liner.

4. The apparatus of claim 1, wherein the aperture has a square shape.

5. A urine collection and drainage apparatus comprising:
a liner having a top surface and a bottom surface, the liner being elongated between a pair of ends;
a pad being coupled to the top surface of the liner, the pad comprising:
a fluid-impermeable layer being configured to prevent urine from a user from leaking therethrough;
an absorbent layer being positioned above the fluid-impermeable layer, the absorbent layer being configured for absorbing the urine, the absorbent layer comprising a cellulose gel; and
a fluid-permeable layer being positioned above the absorbent layer, the fluid-permeable layer being configured for permitting the urine to pass therethrough, the fluid-permeable layer having an aperture extending therethrough, the aperture being centered between the pair of ends of the liner, the aperture having a square shape, the fluid-permeable layer having an inner boundary region surrounding the aperture, the inner boundary region being angled downwardly toward the aperture to form a cavity above and in fluid communication with the aperture;
a filter being coupled to the pad and being positioned in the aperture, the filter being inset downwardly from a top side of the pad, the filter having a plurality of openings extending therethrough, each opening of the plurality of openings having a size such that the filter is configured to permit the urine to pass through the filter and prevent the cellulose gel from passing through the filter;
a drain tube extending through the liner and the pad, the drain tube being in fluid communication with the top side of the pad, the drain tube having an open distal end with respect to the pad, the open distal end having a size such that the open distal end is configured for inserting into an adapter of a suction device such that the drain tube is in fluid communication with the suction device, the drain tube extending through the fluid-impermeable layer and the absorbent layer, the drain tube having an open proximal end with respect to the pad being positioned in abutment with and below the filter; and
a pair of adhesives being coupled to the liner, each adhesive of the pair of adhesives being positioned adjacent to an associated one of the pair of ends of the liner.

* * * * *